United States Patent
Bai et al.

(10) Patent No.: US 12,416,640 B2
(45) Date of Patent: Sep. 16, 2025

(54) METHOD FOR CONTROLLING SPEED OF POLYPEPTIDE PASSING THROUGH NANOPORE AND USE THEREOF

(71) Applicant: TSINGHUA UNIVERSITY, Beijing (CN)

(72) Inventors: Jingwei Bai, Beijing (CN); Zhijie Chen, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 943 days.

(21) Appl. No.: 17/620,338

(22) PCT Filed: Jun. 24, 2020

(86) PCT No.: PCT/CN2020/098190
§ 371 (c)(1),
(2) Date: Dec. 17, 2021

(87) PCT Pub. No.: WO2021/000786
PCT Pub. Date: Jan. 7, 2021

(65) Prior Publication Data
US 2022/0365094 A1 Nov. 17, 2022

(30) Foreign Application Priority Data
Jun. 29, 2019 (CN) .......................... 201910580964.0

(51) Int. Cl.
| | | |
|---|---|---|
| *G01N 33/68* | (2006.01) | |
| *C12Q 1/34* | (2006.01) | |
| *C12Q 1/48* | (2006.01) | |
| *G01N 27/00* | (2006.01) | |
| *G01N 33/558* | (2006.01) | |

(52) U.S. Cl.
CPC ........... *G01N 33/6818* (2013.01); *C12Q 1/34* (2013.01); *C12Q 1/485* (2013.01); *G01N 27/00* (2013.01); *G01N 33/558* (2013.01); *C12Q 2521/513* (2013.01); *C12Q 2565/607* (2013.01); *C12Q 2565/631* (2013.01)

(58) Field of Classification Search
None
See application file for complete search history.

(56) References Cited

U.S. PATENT DOCUMENTS

| | | |
|---|---|---|
| 2016/0146828 A1 | 5/2016 | Lindsay et al. |
| 2016/0209317 A1* | 7/2016 | Bayley ............... G01N 15/1031 |

FOREIGN PATENT DOCUMENTS

| | | |
|---|---|---|
| CN | 1860370 | 11/2006 |
| CN | 104011866 | 8/2014 |
| CN | 104630346 | 5/2015 |
| CN | 105883838 | 8/2016 |
| CN | 106133513 | 11/2016 |
| CN | 108348819 | 7/2018 |
| CN | 109313157 | 2/2019 |

OTHER PUBLICATIONS

International Search Report for PCT/CN2020/098190 dated Oct. 16, 2020, 10 pages.
Written Opinion of the ISA for PCT/CN2020/098190 dated Oct. 16, 2020, 3 pages.

* cited by examiner

*Primary Examiner* — Michelle F. Paguio Frising
(74) *Attorney, Agent, or Firm* — NIXON & VANDERHYE, PC

(57) ABSTRACT

The present invention provides a method for controlling a speed of a polypeptide passing through a nanopore and use thereof in determining an amino acid sequence of a polypeptide. Specifically, the method comprises: conjugating a polynucleotide to the polypeptide to give a polynucleotide-polypeptide conjugate, and applying a voltage across the nanopore in the presence of a polynucleotide binding enzyme to move the conjugate through the nanopore. The polynucleotide binding enzyme controls the movement of the polynucleotide and thereby controls the movement of the conjugated polypeptide in the nanopore, thus controlling the speed of the polypeptide passing through the nanopore.

20 Claims, 7 Drawing Sheets
Specification includes a Sequence Listing.

METHOD FOR CONTROLLING SPEED OF POLYPEPTIDE PASSING THROUGH NANOPORE AND USE THEREOF

CROSS-REFERENCE TO RELATED APPLICATIONS

This application is the U.S. national phase of International Application No. PCT/CN2020/098190 filed Jun. 24, 2020 which designated the U.S. and claims priority to Chinese Patent Application No. 201910580964.0 filed Jun. 29, 2019, the entire contents of each of which are hereby incorporated by reference.

REFERENCE TO SEQUENCE LISTING SUBMITTED ELECTRONICALLY

The content of the electronically submitted sequence listing (Name: 8575-7_Sequence_Listing.txt: Size: 2,440 bytes; and Date of Creation: Dec. 15, 2021) filed with the application on Dec. 17, 2021 is incorporated herein by reference in its entirety.

TECHNICAL FIELD

The present invention relates to the field of protein/polypeptide detection, and in particular to a method for controlling a speed of a polypeptide passing through a nanopore and use thereof in determining an amino acid sequence of a polypeptide.

BACKGROUND

Protein is the physical basis of life and is closely related to various life activities. Characterizing the amino acid sequence and other attributes of the protein is of great meaning to medicine and life science.

Conventional methods for protein sequencing include Edman degradation and mass spectrometry. Patent No. CN106645437A discloses a method for de novo sequencing an amino acid sequence of a polypeptide based on chemical modification and isotope labeling. Patent No. CN104034791A discloses a method for de novo sequencing a polypeptide based on a combination of collision-induced dissociation (CID) and electron transfer dissociation (ETD) mass spectrometry.

Conventional methods for protein sequencing are costly, time-consuming, and complicated to operate. Therefore, there is an urgent need for a protein sequencing and detection method of high throughput and cost-efficiency.

Nanopore analysis is a cost-efficient, fast, and label-free single-molecule detection technology, and has been successfully applied in the field of polynucleotide sequencing.

The nanopore sequencing method utilizes electrophoresis technology to drive individual DNA or RNA molecules through a nanopore one by one to implement the sequencing. Patent No. CN104694649A discloses a nanopore-based polynucleotide sequencing method with a low passing speed and a special nanopore device. Patent No. CN106255551A discloses a method and device for long-read, label-free optical nanopore linear molecule sequencing. Patent No. CN108885649A discloses a method for rapid sequencing of short DNA fragments using nanopore technology.

On the other hand, a key factor for nanopore technology to implement polynucleotide sequencing is to find a suitable polynucleotide binding enzyme, such as synthetase or helicase, which can move along the backbone of the linear polynucleotide polymer, thereby effectively controlling the speed of polynucleotide passing through the nanopore. Therefore, finding suitable enzymes that can control the speed of the polypeptide passing through the nanopore is the key to the nanopore sequencing of peptide. At present, no suitable enzyme that directly acts on polypeptide chains and uniformly controls the speed of the polypeptide chain passing through the nanopore has yet been found. The present invention provides a method for directing proteins/polypeptides through nanopores and acquiring electrical signals. Specifically, a polynucleotide is conjugated to a polypeptide, and the passing of the polypeptide through the nanopore is indirectly controlled by a polynucleotide binding enzyme that controls the polynucleotide. The electrical signal acquired by the method can be further used to determine the amino acid sequence of the polypeptide or to characterize other attributes of the polypeptide.

SUMMARY

The present invention provides a method for controlling a speed of protein/polypeptide passing through a nanopore by enzymes. Specifically, a polynucleotide is conjugated to the polypeptide, and a polynucleotide binding enzyme controls the movement of the polynucleotide and thereby controls the movement of the conjugated polypeptide in the nanopore, thus controlling the speed of the polypeptide passing through the nanopore. While controlling the speed of the polypeptide, the present invention reads a nanopore current signal during the process of the polypeptide passing through the nanopore to acquire an electrical signal of the polypeptide. The electrical signal can be further used to acquire an amino acid sequence of the test polypeptide, or to identify the test polypeptide or a part thereof, for example, to identify mutation sites or polypeptide/protein post-translational modifications. The method disclosed herein can also be used to determine the electrical signals of known polypeptides to establish a library of polypeptide signals.

The first aspect of the present invention relates to a method for controlling a speed of a polypeptide passing through a nanopore by an enzyme, comprising:
 1) conjugating the polypeptide to a polynucleotide to give a polynucleotide-polypeptide conjugate; and
 2) applying a voltage across the nanopore in the presence of a polynucleotide binding enzyme to move the polynucleotide-polypeptide conjugate through the nanopore, wherein the polynucleotide binding enzyme controls the movement of the polynucleotide, thus indirectly controlling the speed of the conjugated polypeptide passing through the nanopore (passing speed).

The polynucleotide binding enzyme includes polymerase, helicase and translocase, preferably helicase.

In one embodiment of the present invention, the polynucleotide binding enzyme is a polymerase, preferably phi29.

In another embodiment of the present invention, the polynucleotide binding enzyme is a translocase.

In yet another embodiment of the present invention, the polynucleotide binding enzyme is a helicase, preferably a helicase capable of directing the polynucleotide in a direction against electric field force, more preferably a helicase from the Hel308 family, including Hel308 Tga or a sequence of a variant thereof, Hel308 Mbu or a sequence of a variant thereof, Hel308 Pfu or a sequence of a variant thereof, Hel308Mma or a sequence of a variant thereof, Hel308Mok or a sequence of a variant thereof, Hel308Fac or a sequence of a variant thereof, Hel308Csy or a sequence of a variant thereof, Hel308Mhu or a sequence of a variant thereof, and F8813 protein or a sequence of a variant thereof.

In yet another embodiment of the present invention, the voltage across the nanopore is applied in the presence of an antisense polynucleotide of the polynucleotide and a helicase.

Preferably, the polynucleotide in step 1) is a DNA or RNA. Further preferably, the polynucleotide is a DNA. More preferably, the polynucleotide is a single-stranded DNA.

The polynucleotide and the polypeptide in step 1) can be conjugated in any manner known in the art. For example, the polynucleotide and the polypeptide are linked covalently or through a linker group to form the polynucleotide-polypeptide conjugate. The covalent linkage of the polynucleotide and the polypeptide is in a manner including, but not limited to, an oxime bond, an amide bond, a thioether bond, a disulfide bond, a phosphoryl bond, a hydrazone bond, and a ureide bond, and a cyclic linkage formed by click reaction. Specific preparation methods for covalently linking the polynucleotide and the polypeptide are described in, for example, "Chemical Strategies for the Synthesis of Peptide-Oligonucleotide Conjugates, K. Lu, et al., Bioconjugate chemistry, 2009, ACS Publications".

In one embodiment of the present invention, the polynucleotide and the polypeptide are conjugated through reductive amination between an N-terminal amino group of the polypeptide and an aldehyde group modification of the polynucleotide in a weakly acidic condition. In another embodiment of the present invention, for a peptide chain with a cysteine at one end, a maleamide-NHS double crosslinking reagent, such as sulfosuccinimidyl 4-(N-maleimidomethyl) cyclohexane-1-carboxylate (Sulfo-SMCC), is preferably used for conjugating a DNA with an amino group.

Preferably, the nanopore is a biological nanopore. Further preferably, the nanopore is an MspA nanopore.

The second aspect of the present invention relates to a method for determining an electrical signal of a polypeptide, comprising:
1) conjugating the polypeptide to a polynucleotide to give a polynucleotide-polypeptide conjugate;
2) applying a voltage across the nanopore in the presence of a polynucleotide binding enzyme to move the polynucleotide-polypeptide conjugate through the nanopore, wherein the polynucleotide binding enzyme controls the movement of the polynucleotide, thus controlling the passing speed of the conjugated polypeptide; and 3) reading a nanopore current signal to acquire the electrical signal of the polypeptide.

In one embodiment of the present invention, the polynucleotide binding enzyme is a polymerase, preferably phi29.

In another embodiment of the present invention, the polynucleotide binding enzyme is a translocase. In yet another embodiment of the present invention, the polynucleotide binding enzyme is a helicase, preferably a helicase capable of directing the polynucleotide in a direction against electric field force, more preferably a helicase from the Hel308 family, including Hel308 Tga or a sequence of a variant thereof, Hel308 Mbu or a sequence of a variant thereof, Hel308 Pfu or a sequence of a variant thereof, Hel308Mma or a sequence of a variant thereof, Hel308Mok or a sequence of a variant thereof, Hel308Fac or a sequence of a variant thereof, Hel308Csy or a sequence of a variant thereof, Hel308Mhu or a sequence of a variant thereof, and F8813 protein or a sequence of a variant thereof.

In yet another embodiment of the present invention, the voltage across the nanopore is applied in the presence of an antisense polynucleotide of the polynucleotide and a helicase. Preferably, the polynucleotide in step 1) is a DNA or RNA. Further preferably, the polynucleotide is a DNA. More preferably, the polynucleotide is a single-stranded DNA.

The polynucleotide and the polypeptide in step 1) can be conjugated in any manner known in the art. For example, the polynucleotide and the polypeptide are linked covalently or through a linker group to form the polynucleotide-polypeptide conjugate. The covalent linkage of the polynucleotide and the polypeptide is in a manner including, but not limited to, an oxime bond, an amide bond, a thioether bond, a disulfide bond, a phosphoryl bond, a hydrazone bond, and a ureide bond, and a cyclic linkage formed by click reaction.

In one embodiment of the present invention, the polynucleotide and the polypeptide are conjugated through reductive amination between an N-terminal amino group of the polypeptide and an aldehyde group modification of the polynucleotide in a weakly acidic condition. In another embodiment of the present invention, for a peptide chain with a cysteine at one end, a maleamide-NHS double crosslinking reagent, such as sulfosuccinimidyl 4-(N-maleimidomethyl) cyclohexane-1-carboxylate (Sulfo-SMCC), is preferably used for conjugating a DNA with an amino group.

Preferably, the nanopore is a biological nanopore. Further preferably, the nanopore is an MspA nanopore.

In one specific embodiment of the present invention, the method comprises:
1) activating an ssDNA with Sulfo-SMCC, and adding a polypeptide containing a sulfhydryl group at one end to give an ssDNA-polypeptide conjugate:
2) mixing the ssDNA-polypeptide conjugate with an antisense ssDNA (ssDNA-R), and annealing the mixture to form a double-stranded part:
3) preparing a phospholipid bilayer embedded with a single porin; and
4) adding the annealed product from step 2), a helicase, ATP and magnesium ion, applying a voltage, and recording a generated electrical signal.

The third aspect of the present invention relates to a method for determining an amino acid sequence of a polypeptide, comprising:
1) conjugating the polypeptide to a polynucleotide to give a polynucleotide-polypeptide conjugate:
2) applying a voltage across the nanopore in the presence of a polynucleotide binding enzyme to move the polynucleotide-polypeptide connection product through the nanopore, wherein the polynucleotide binding enzyme controls the movement of the polynucleotide, thus indirectly controlling the passing speed of the conjugated polypeptide; and
3) reading a nanopore current signal to identify a current signal of the amino acid sequence of the polypeptide.

In one embodiment of the present invention, the polynucleotide binding enzyme is a polymerase, preferably phi29.

In another embodiment of the present invention, the polynucleotide binding enzyme is a translocase.

In yet another embodiment of the present invention, the polynucleotide binding enzyme is a helicase, preferably a helicase capable of directing the polynucleotide in a direction against electric field force, more preferably a helicase from the Hel308 family, including Hel308 Tga or a sequence of a variant thereof, Hel308 Mbu or a sequence of a variant thereof, Hel308 Pfu or a sequence of a variant thereof, Hel308Mma or a sequence of a variant thereof, Hel308Mok or a sequence of a variant thereof, Hel308Fac or a sequence of a variant thereof, Hel308Csy or a sequence of a variant thereof, Hel308Mhu or a sequence of a variant thereof, and F8813 protein or a sequence of a variant thereof.

In yet another embodiment of the present invention, the voltage across the nanopore is applied in the presence of an antisense polynucleotide of the polynucleotide and a helicase.

Preferably, the polynucleotide in step 1) is a DNA or RNA. Further preferably, the polynucleotide is a DNA. More preferably, the polynucleotide is a single-stranded DNA.

The polynucleotide and the polypeptide in step 1) can be conjugated in any manner known in the art. For example, the polynucleotide and the polypeptide are linked covalently or through a linker group to form the polynucleotide-polypeptide conjugate. The covalent linkage of the polynucleotide and the polypeptide is in a manner including, but not limited to, an oxime bond, an amide bond, a thioether bond, a disulfide bond, a phosphoryl bond, a hydrazone bond, and a ureide bond, and a cyclic linkage formed by click reaction.

In one embodiment of the present invention, the polynucleotide and the polypeptide are conjugated through reductive amination between an N-terminal amino group of the polypeptide and an aldehyde group modification of the polynucleotide in a weakly acidic condition. In another embodiment of the present invention, for a peptide chain with a cysteine at one end, a maleamide-NHS double crosslinking reagent, such as sulfosuccinimidyl 4-(N-maleimidomethyl) cyclohexane-1-carboxylate (Sulfo-SMCC), is preferably used for conjugating a DNA with an amino group.

Preferably, the nanopore in step 2) is a biological nanopore. Further preferably, the nanopore is an MspA nanopore.

The fourth aspect of the present invention relates to a method for identifying a polypeptide or a part thereof, comprising:
1) conjugating the polypeptide to a polynucleotide to give a polynucleotide-polypeptide conjugate;
2) applying a voltage across the nanopore in the presence of a polynucleotide binding enzyme to move the polynucleotide-polypeptide connection product through the nanopore, wherein the polynucleotide binding enzyme controls the movement of the polynucleotide, thus indirectly controlling the passing speed of the conjugated polypeptide;
3) reading a nanopore current signal to acquire an electrical signal of the polypeptide; and 4) identifying the polypeptide or the part thereof based on the electrical signal.

In one embodiment of the present invention, the polynucleotide binding enzyme is a polymerase, preferably phi29.

In another embodiment of the present invention, the polynucleotide binding enzyme is a translocase.

In yet another embodiment of the present invention, the polynucleotide binding enzyme is a helicase, preferably a helicase capable of directing the polynucleotide in a direction against electric field force, more preferably a helicase from the Hel308 family, including Hel308 Tga or a sequence of a variant thereof, Hel308 Mbu or a sequence of a variant thereof, Hel308 Pfu or a sequence of a variant thereof, Hel308Mma or a sequence of a variant thereof, Hel308Mok or a sequence of a variant thereof, Hel308Fac or a sequence of a variant thereof, Hel308Csy or a sequence of a variant thereof, Hel308Mhu or a sequence of a variant thereof, and F8813 protein or a sequence of a variant thereof. Preferably, the polynucleotide in step 1) is a DNA or RNA. Further preferably, the polynucleotide is a DNA. More preferably, the polynucleotide is a single-stranded DNA.

In yet another embodiment of the present invention, the voltage across the nanopore is applied in the presence of an antisense polynucleotide of the polynucleotide and a helicase. The polynucleotide and the polypeptide in step 1) can be conjugated in any manner known in the art. For example, the polynucleotide and the polypeptide are linked covalently or through a linker group to form the polynucleotide-polypeptide conjugate. The covalent linkage of the polynucleotide and the polypeptide is in a manner including, but not limited to, an oxime bond, an amide bond, a thioether bond, a disulfide bond, a phosphoryl bond, a hydrazone bond, and a ureide bond, and a cyclic linkage formed by click reaction.

In one embodiment of the present invention, the polynucleotide and the polypeptide are conjugated through reductive amination between an N-terminal amino group of the polypeptide and an aldehyde group modification of the polynucleotide in a weakly acidic condition. In another embodiment of the present invention, for a peptide chain with a cysteine at one end, a maleamide-NHS double crosslinking reagent, such as sulfosuccinimidyl 4-(N-maleimidomethyl) cyclohexane-1-carboxylate (Sulfo-SMCC), is preferably used for conjugating a DNA with an amino group.

Preferably, the nanopore is a biological nanopore. Further preferably, the nanopore is an MspA nanopore.

The identification of the polypeptide or the part thereof in step 4) can be performed by any method known in the art, for example, by comparing the acquired amino acid sequence of the polypeptide with a database.

In one specific embodiment of the present invention, the electrical signals of known polypeptides are determined and a library of determined signals is established, before the electrical signal of the polypeptide is compared with the signal library to implement the identification of the polypeptide or the part thereof.

The identification described herein can be a detection of a post-translational modification in the polypeptide or the part thereof. The modification is preferably selected from ubiquitination, phosphorylation, glycosylation, esterification, alkylation and acetylation, glutamation, lipoation, isoprenylation, glycination, sulfation, adenylation and ADP ribosylation.

The fifth aspect of the present invention relates to a method for establishing a library of polypeptide identification signals. Specifically, known polypeptides are directed through a nanopore sensor, and electrical signals are collected to acquire electrical signals. In one specific embodiment, the method comprises:
1) conjugating a known polypeptide to a polynucleotide to give a polynucleotide-polypeptide conjugate:
2) applying a voltage across the nanopore in the presence of a polynucleotide binding enzyme to move the polynucleotide-polypeptide connection product through the nanopore, wherein the polynucleotide binding enzyme controls the movement of the polynucleotide, thus indirectly controlling the passing speed of the conjugated polypeptide:
3) reading a nanopore current signal to acquire the electrical signal of the known polypeptide; and
4) establishing a library of polypeptide identification signals using the electrical signal of the known polypeptide from step 3).

In one embodiment of the present invention, the polynucleotide binding enzyme is a polymerase, preferably phi29.

In another embodiment of the present invention, the polynucleotide binding enzyme is a translocase.

In yet another embodiment of the present invention, the polynucleotide binding enzyme is a helicase, preferably a helicase capable of directing the polynucleotide in a direction against electric field force, more preferably a helicase from the Hel308 family, including Hel308 Tga or a sequence of a variant thereof, Hel308 Mbu or a sequence of a variant thereof, Hel308 Pfu or a sequence of a variant thereof, Hel308Mma or a sequence of a variant thereof, Hel308Mok or a sequence of a variant thereof, Hel308Fac or a sequence of a variant thereof, Hel308Csy or a sequence of a variant thereof, Hel308Mhu or a sequence of a variant thereof, and F8813 protein or a sequence of a variant thereof.

In yet another embodiment of the present invention, the voltage across the nanopore is applied in the presence of an antisense polynucleotide of the polynucleotide and a helicase.

Preferably, the polynucleotide in step 1) is a DNA or RNA. Further preferably, the polynucleotide is a DNA. More preferably, the polynucleotide is a single-stranded DNA.

The polynucleotide and the polypeptide in step 1) can be conjugated in any manner known in the art. For example, the polynucleotide and the polypeptide are linked covalently or through a linker group to form the polynucleotide-polypeptide conjugate. The covalent linkage of the polynucleotide and the polypeptide is in a manner including, but not limited to, an oxime bond, an amide bond, a thioether bond, a disulfide bond, a phosphoryl bond, a hydrazone bond, and a ureide bond, and a cyclic linkage formed by click reaction.

In one embodiment of the present invention, the polynucleotide and the polypeptide are conjugated through reductive amination between an N-terminal amino group of the polypeptide and an aldehyde group modification of the polynucleotide in a weakly acidic condition. In another embodiment of the present invention, for a peptide chain with a cysteine at one end, a maleamide-NHS double crosslinking reagent, such as sulfosuccinimidyl 4-(N-maleimidomethyl) cyclohexane-1-carboxylate (Sulfo-SMCC), is preferably used for conjugating a DNA with an amino group.

Preferably, the nanopore is a biological nanopore. Further preferably, the nanopore is an MspA nanopore.

The term "polynucleotide" used herein refers to a polymer or oligomer consisting of one or more nucleotides. The polynucleotide may include a DNA polynucleotide or oligonucleotide, an RNA polynucleotide or oligonucleotide, or one or more parts of a DNA polynucleotide or oligonucleotide and/or an RNA polynucleotide or oligonucleotide. As generally used herein, "nucleotide" or "base" may be a basic nucleotide or a nucleotide analogue. The basic nucleotide is deoxyadenosine monophosphate (dAMP), deoxycytidine monophosphate (dCMP), deoxyguanosine monophosphate (dGMP), deoxythymidine monophosphate (dTMP), adenosine monophosphate (AMP), cytosine monophosphate (CMP), guanosine monophosphate (GMP) or uridine monophosphate (UMP). Nucleotide analogues are analogues or mimetics of basic nucleotides with modifications on the basic nucleobases (A, C, G, T and U), deoxyribose/ribose structures, the phosphate groups of basic nucleotides, or any combination thereof. For example, nucleotide analogues may have modified bases, either naturally occurring or artificial. Examples of modified bases include, but are not limited to, methylated nucleobases, modified purine bases (e.g., hypoxanthine, xanthine, 7-methylguanine, isodG), modified pyrimidine bases (e.g., 5,6-dihydrouracil and 5-methylcytosine, isodC), universal bases (e.g., 3-nitropyrrole and 5-nitroindole), non-binding base mimetics (For example, 4-methylbenzimidazole and 2,4-difluorotoluene or benzene) and abasic sites (abasic nucleotides, where the nucleotide analogue does not contain a base). Examples of analogues of nucleotides with modified deoxyribose (for example, dideoxynucleosides, such as dideoxyguanosine, dideoxyadenosine, dideoxythymidine, and dideoxycytidine) and/or phosphate structures (collectively referred to as backbone structures) include, but are not limited to, glycol nucleotides, morpholinos, and locked nucleotides.

The term "nanopore" used herein may be a biological nanopore or a solid nanopore. Examples of biological nanopores include, but are not limited to, *Staphylococcus aureus* α-hemolysin nanopore, MspA nanopore, Csgg nanopore, phi29 nanopore, FraC nanopore and various other naturally occurring, modified natural and synthetic nanopores consisting of biological macromolecules. Examples of solid nanopores include, but are not limited to, silicon nitride nanopores, titanium dioxide nanopores, aluminum oxide nanopores, graphene nanopores. Appropriate nanopores can be selected based on the properties of the polypeptide.

The term "antisense polynucleotide" used herein refers to a polynucleotide that can be annealed with the polynucleotide to form a double-stranded polynucleotide. The antisense polynucleotide can be completely mated with the polynucleotide or partially mated with the polynucleotide. Those capable of forming a double-stranded structure with the polynucleotide by annealing and controlling the speed of the polynucleotide and the conjugated polypeptide passing through the nanopore in the action of a helicase are "antisense polynucleotides" of the present invention.

The term "part" used herein may be a continuous amino acid sequence of the polypeptide such as a conservative sequence or motif, or one or more amino acid residues such as one or more mutation sites of the polypeptide.

The term "polynucleotide binding enzyme" used herein includes polymerase, helicase and translocase, preferably helicase.

The term "polymerase" used herein may be phi29 (*Bacillus* phage φ29) or a variant thereof, pol6 (*Clostridium* phage phiCPV4; GenBank: AFH27113.1) or a variant thereof, or pol7 (*Actinomyces* phage Av-1: GenBank: ABR67671.1) or a variant thereof.

The term "helicase" used herein can be selected from Hel308 helicase (e.g., TraI helicase and TrwC helicase), RecD helicase, XPD helicase and Dda helicase. The helicase can be Hel308 Tga or a sequence of a variant thereof, Hel308 Mbu or a sequence of a variant thereof, Hel308 Pfu or a sequence of a variant thereof, Hel308Mma or a sequence of a variant thereof, Hel308Mok or a sequence of a variant thereof, Hel308Fac or a sequence of a variant thereof, Hel308Csy or a sequence of a variant thereof, Hel308Mhu or a sequence of a variant thereof, or F8813 protein or a sequence of a variant thereof. Also, the helicase can be any one of the helicases, modified helicases, or helicase constructs disclosed in the following international application Nos: PCT/GB2012/052579, PCT/GB2012/053274, PCT/GB2012/053273, PCT/GB2013/051925, PCT/GB2013/051924, PCT/GB2013/051928, PCT/GB2014/052736, PCT/GB2014/052736, PCT/GB2015/052916 and PCT/CN2018/108227.

DESCRIPTION OF THE DRAWINGS

Hereinafter, embodiments of the present invention will be described in detail with reference to the accompanying drawings, in which.

DETAILED DESCRIPTION

Technical schemes in the examples of the present invention will be described clearly and completely in conjunction with the accompanying drawings. It is apparent that the examples described herein are only some examples of the present invention, but not all of them. Based on the examples of the present invention, all other examples obtained by those of ordinary skill in the art without creative work shall fall within the protection scope of the present invention.

Example 1. Materials

Hel308 helicase, ATP (100 mM, Thermo Fisher)
1,2-Diphytanoyl-sn-glycero-3-phosphocholine (Avanti)
Sequences:

```
ssDNA (SEQ ID NO. 1):
NH2-CAAGAATACCTTTTTTTTCCTTTTTTTCCTCTACCACTTTTCAG

ATCTCACTATCGCATTCTCATGCAGGTCGTAGCTTTTTCTTTTTCATC

ATC ssDNA-R (SEQ ID NO. 2):
TTTTTTTTTTTTTTTGCTACGACCTGCATGAGAATTTTTTTTTTTTTT

TTTTTTTTTTTTTTTTTTTTT-cholesterol

EGSLFL-60C (SEQ ID NO. 3):
EEEEGEEEEGGEEEGGEEESSEEEEGGEEELFEEGGGGEEEESSSSEEEE

LLEEEEEEC

EDSLFYD-60C (SEQ ID NO. 4):
EDEDEEEDYDDDEEEDEEDEVEEEEEYGEVVGELGGGGSHHDHHSSSGSE

EEYEEDDDDC
```

```
-continued
E29C (SEQ ID NO. 5):
EEEEEEEEEEEEEEEEEEEEEEEEEEEEC
```

Example 2. Determination of ssDNA

1. Procedures:

The ssDNA and ssDNA-R in Example 1 were annealed at a molar ratio of 1:1 to form a double-stranded part: the cross section of PEEK tubing was pre-coated with a mixture of phospholipid and hexadecane and immersed in an electrolyte solution before bubbles were blown on the cross section of the peek tubing and sucked away using a pipette to form a phospholipid bilayer. In a system of 400 mM KCl in HEPES buffer (pH 7), MspA protein was added at the cis terminal. At 180 mV, when a pore current of about 160 pA was read, a 2-µL mixture of the above-mentioned annealed product and Hel308 protein was added to 50 µL of the cis terminal solution before adding 2 µL of ATP. A voltage of 180 mV was applied and the data were recorded.

2. Results

Figure 1:
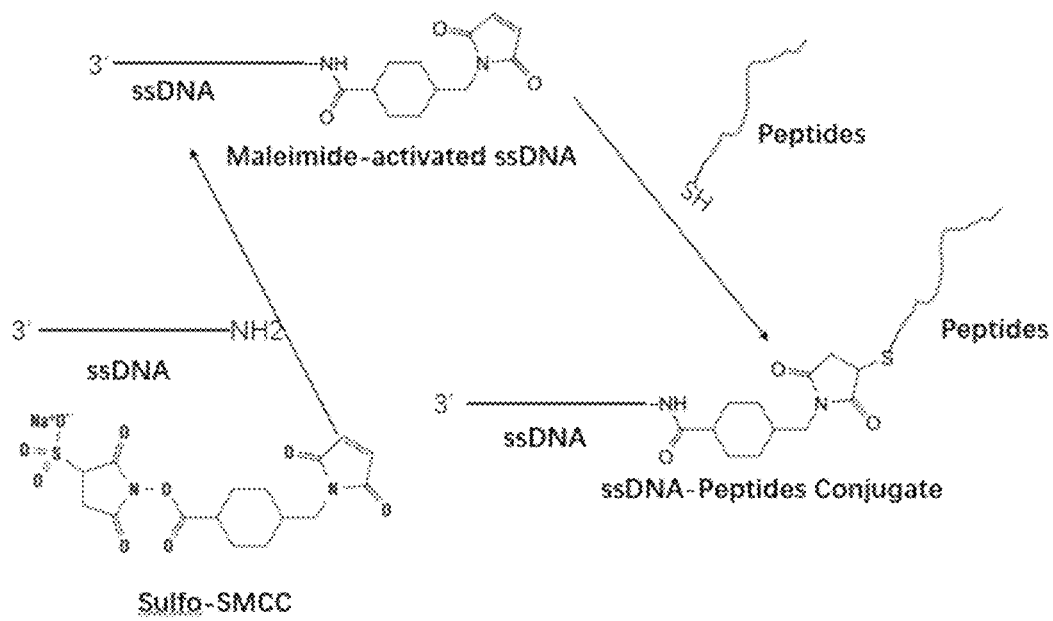
FIG. 1 illustrates an ssDNA-polypeptide conjugate formed by conjugating a Sulfo-SMCC-activated ssDNA and a polypeptide with a sulfhydryl group at one end.
Figure 2:
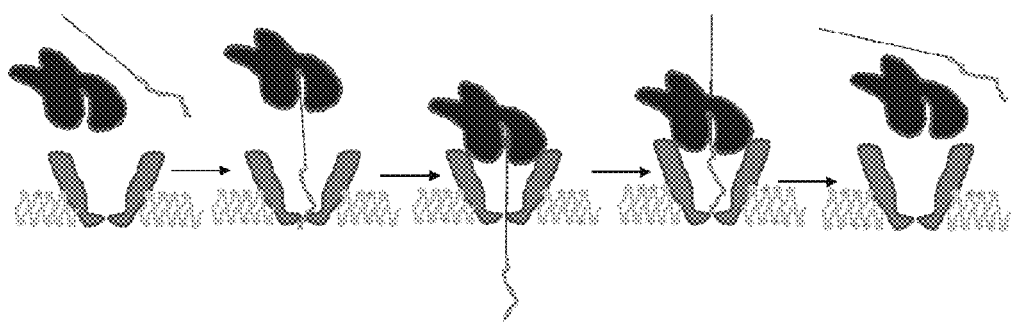
FIG. 2 illustrates the process of the ssDNA-polypeptide conjugate passing through a nanopore in the presence of a polynucleotide binding enzyme: the polynucleotide-polypeptide conjugate quickly passes through the nanopore, and in the action of the polynucleotide binding enzyme, the polynucleotide pulls the conjugated polypeptide to pass through the nanopore again at a controlled speed, and when the polypeptide passes through the nanopore, the polypeptide is determined.
Figure 3:
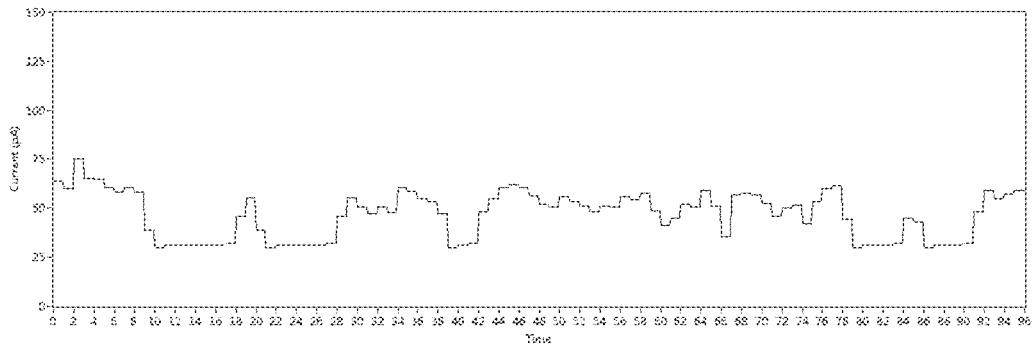
FIG. 3 illustrates a predicted ssDNA test signal.
Figure 4:
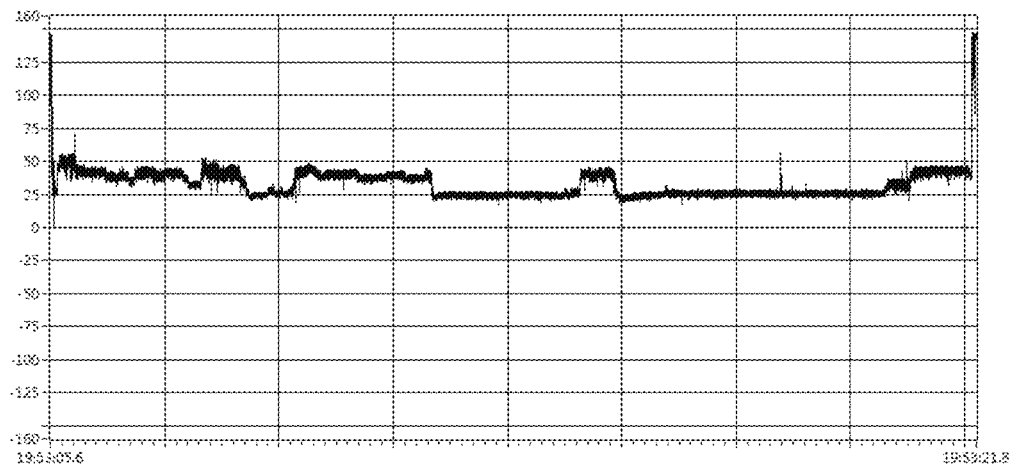
FIG. 4 illustrates an actual ssDNA test result.
Figure 5:
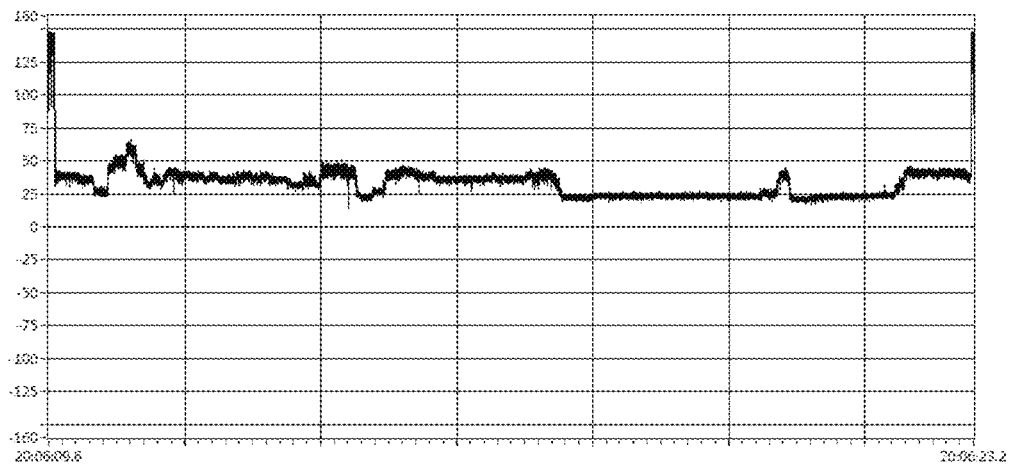
FIG. 5 illustrates an actual ssDNA test result.
Figure 6:
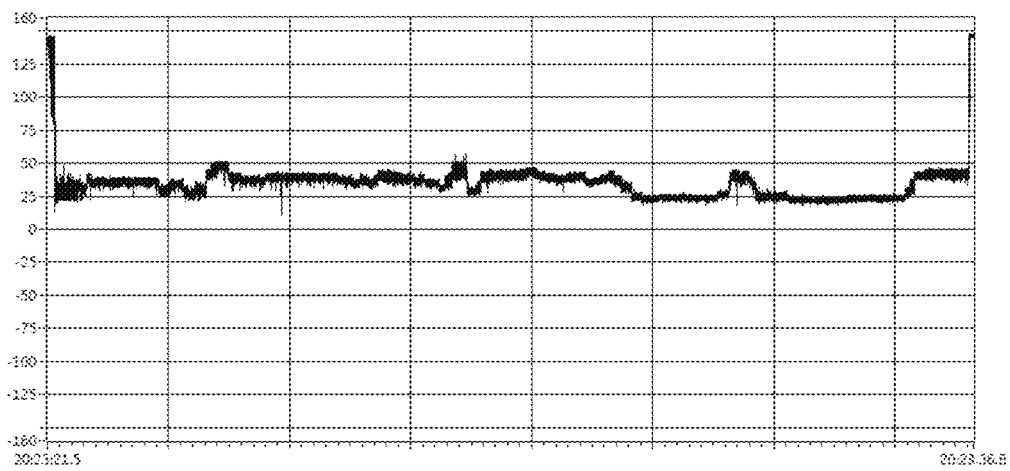
FIG. 6 illustrates an actual ssDNA test result.

As shown in FIGS. 4, 5 and 6, nanopore current demonstrated stepped jumps over time at a fixed voltage, which is the passing current signal of the ssDNA under the speed control of the helicase. In particular, long step signals of about 25 pA were observed in the second half of these segments, in which a rising current step was also observed. Such changes are consistent with the passing signal of positions 80-90 in the nucleotide sequence in FIG. 3, corresponding to the passing signal of TTTTTTTTTCCTTTTTTTT sequence near the 5' end of the ssDNA.

Example 3. Conjugation of ssDNA and Polypeptide

1. Procedures:

1 mg of Sulfo-SMCC was dissolved in 40 µL DMSO. After a complete dissolution, 80 µL of 150 mM boric acid buffer (pH 8.5) was added and mixed well. The mixture was quickly added to 10-16 nmol of ssDNA in Example 1, vortexed and shaken to mix well, and incubated in a thermostat at 30° C. Unchanged SMCC was removed by dialysis, ethanol precipitation and desalting column. According to the ssDNA concentration measured by UV absorption, sulfhydryl-containing polypeptides EGSLFL-60C, EDSLFYD-60C and E29C at a 5-fold concentration were added, and shaken at room temperature for 1.5 h. The products were preserved at −20° C. for later use. The above conjugate was used for 15% Urea-PAGE gel electrophoresis.

2. Results

Figure 7:
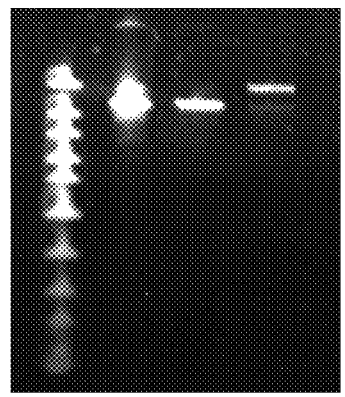
FIG. 7 illustrates a 15% denaturing gel electrophoresis of the ssDNA-polypeptide conjugate, wherein lanes 2-4 are ssDNA, ssDNA+Sulfo-SMCC, ssDNA+Sulfo-SMCC+E29C, respectively.
Figure 8:
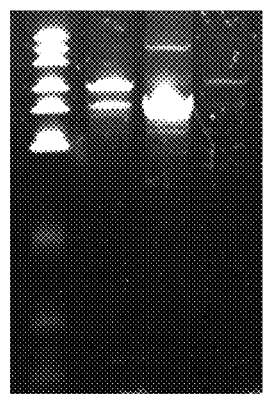
FIG. 8 illustrates a 15% denaturing gel electrophoresis of the ssDNA-polypeptide conjugate, wherein lanes 2-4 are ssDNA+Sulfo-SMCC+EGSLFL-60C, ssDNA, and SSDNA+Sulfo-SMCC+EDSLFYD-60C, respectively.

FIGS. 7 and 8 show the 15% Urea-PAGE gel electrophoresis results of the ssDNA-polypeptide conjugate. Lanes 2-4 in FIG. 7 were ssDNA, ssDNA+Sulfo-SMCC, ssDNA+Sulfo-SMCC+E29C, respectively. Lanes 2-4 in FIG. 8 were ssDNA+Sulfo-SMCC+EGSLFL-60C, ssDNA, ssDNA+Sulfo-SMCC+EDSLFYD-60C, respectively. The bands in the figures were all in the desired positions. Among these, high molecular weight bands were observed after conjugation to peptide chains, indicating a successful ssDNA-polypeptide conjugation and a reaction efficiency above 50% for the ssDNA part. The high molecular weight band with low signal intensity in Lane 3 ssDNA sample of FIG. 8 was caused by excessive sample amount, rather than the conjugate.

Example 4. Determination of ssDNA-E29C Conjugate

1. Procedures:

The ssDNA-E29C conjugate from Example 3 and ssDNA-R were annealed at a molar ratio of 1:1 to form a double-stranded part: the cross section of PEEK tubing was pre-coated with a mixture of phospholipid and hexadecane and immersed in an electrolyte solution before bubbles were blown on the cross section of the peek tubing and sucked away using a pipette to form a phospholipid bilayer. In a system of 400 mM KCl in HEPES buffer (pH 7), MspA protein was added at the cis terminal. At 180 mV, when a pore current of about 160 pA was read, a 2-μL mixture of the above-mentioned annealed product and Hel308 protein was added to 50 μL of the cis terminal solution before adding 2 μL of ATP. A voltage of 180 mV was applied and the data were recorded.

2. Results

Figure 9:
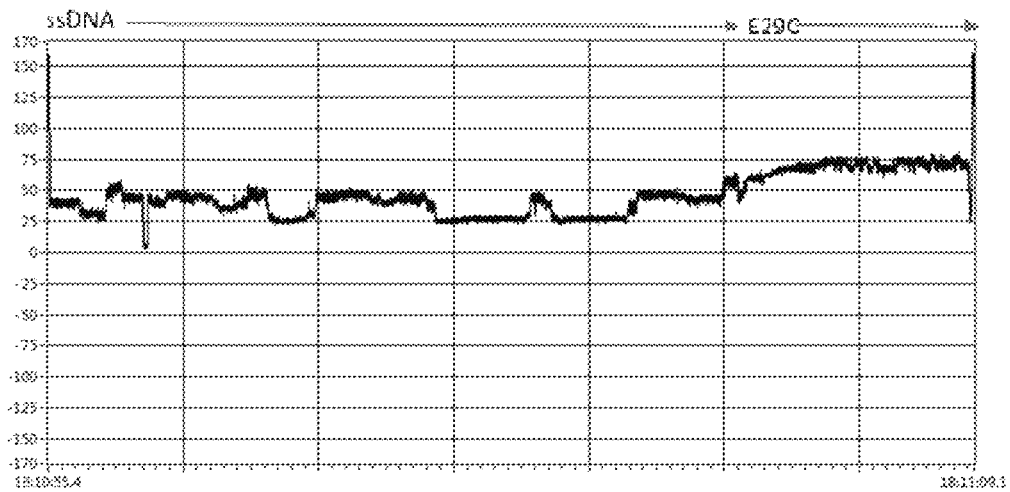
FIGS. 9-10 illustrate test results of the conjugate of ssDNA and E29C.
Figure 10:
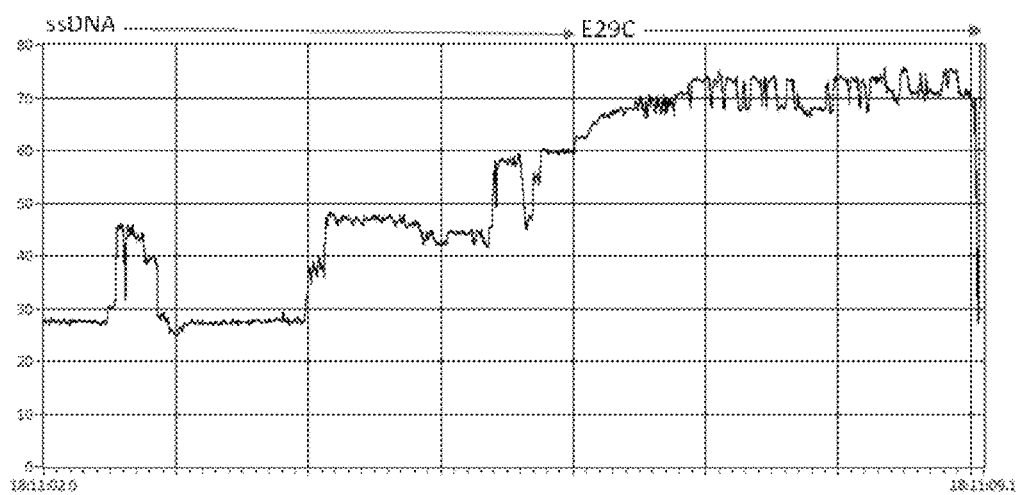

As shown in FIG. 9, the ssDNA-E29C conjugate first demonstrated a current signal similar to those in FIGS. 7 and 8, indicating a controlled passing-through of the ssDNA part, and then a fluctuating plateau at 70-75 pA at the end of the signal was observed. As the current generated by ssDNA in the nanopore in this condition was below 60 pA, this high current value was caused by the peptide chain being dragged into the narrowest part of the nanopore. In a straightened state, the peptide chain has a smaller diameter than ssDNA, thus generating a larger nanopore current. FIG. 10 is an enlarged view of the signal in FIG. 9 where the peptide chain passed through the nanopore. It can be seen that the 70-75 pA plateau had a nearly 5-pA fluctuation, which may be caused by the thermal movement of the E29 peptide chain during the passing.

Example 5. Determination of ssDNA-EGSLFL-60Cconjugate

1. Procedures:

The ssDNA-EGSLFL-60C conjugate from Example 3 and ssDNA-R were annealed at a molar ratio of 1:1 to form a double-stranded part: the cross section of PEEK tubing was pre-coated with a mixture of phospholipid and hexadecane and immersed in an electrolyte solution before bubbles were blown on the cross section of the peek tubing and sucked away using a pipette to form a phospholipid bilayer. In a system of 400 mM KCl in HEPES buffer (pH 7), MspA protein was added at the cis terminal. At 180 mV, when a pore current of about 160 pA was read, a 2-μL mixture of the above-mentioned annealed product and Hel308 protein was added to 50 μL of the cis terminal solution before adding 2 μL of ATP. A voltage of 180 mV was applied and the data were recorded.

2. Results

Figure 11:
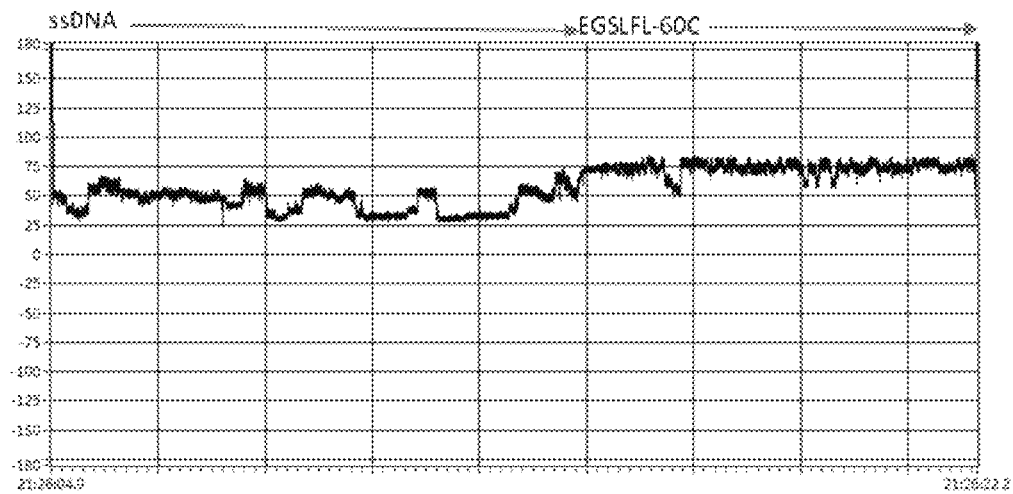
FIGS. 11-12 illustrate test results of the conjugate of ssDNA and EGSLFL-60C.
Figure 12:
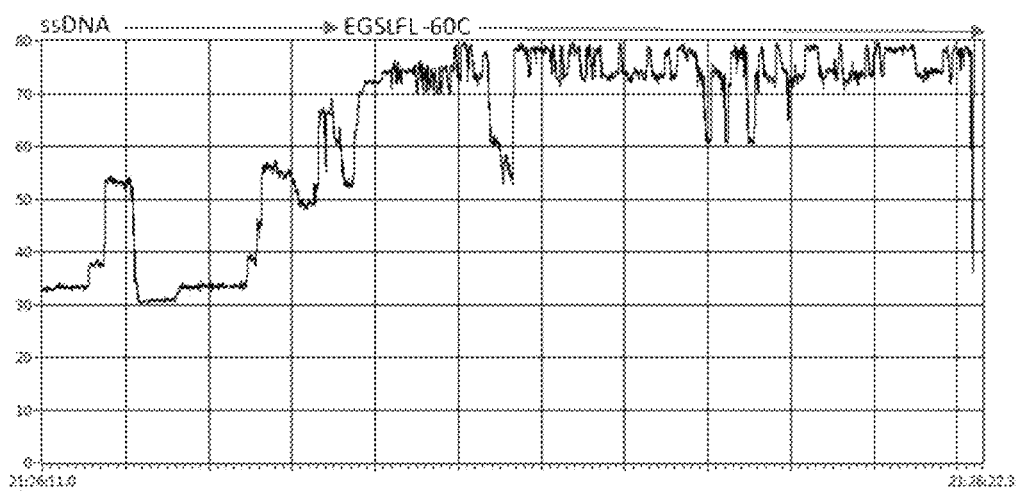

As shown in FIG. 11, the ssDNA-EGSLFL-60C conjugate first demonstrated a current signal similar to those in FIGS. 7 and 8, indicating a controlled passing-through of the ssDNA part, and then a fluctuating plateau at 70-75 pA at the end of the signal was observed. As the current generated by ssDNA in the nanopore in this condition was below 60 pA, this high current value was caused by the peptide chain being dragged into the narrowest part of the nanopore. In a straightened state, the peptide chain has a smaller diameter than ssDNA, thus generating a larger nanopore current. FIG. 12 is an enlarged view of the signal in FIG. 11 where the peptide chain passed through the nanopore. It can be seen that a current trough of nearly 50 pA was observed at the beginning of the 70-75 pA plateau, which may be caused by the current decrease due to the hydrophobic amino acid LL near the C-terminal. This indicates that the method can distinguish amino acid sequences to a certain extent.

Example 6. Determination of ssDNA-EDSLFYD-60Cconjugate

1. Procedures:

The ssDNA-EDSLFYD-60C conjugate from Example 3 and ssDNA-R were annealed at a molar ratio of 1:1 to form a double-stranded part: the cross section of PEEK tubing was pre-coated with a mixture of phospholipid and hexadecane and immersed in an electrolyte solution before bubbles were blown on the cross section of the peek tubing and sucked away using a pipette to form a phospholipid bilayer. In a system of 400 mM KCl in HEPES buffer (pH 7), MspA protein was added at the cis terminal. At 180 mV, when a pore current of about 160 pA was read, a 2-μL mixture of the above-mentioned annealed product and Hel308 protein was added to 50 μL of the cis terminal solution before adding 2 μL of ATP. A voltage of 180 mV was applied and the data were recorded.

2. Results

Figure 13:
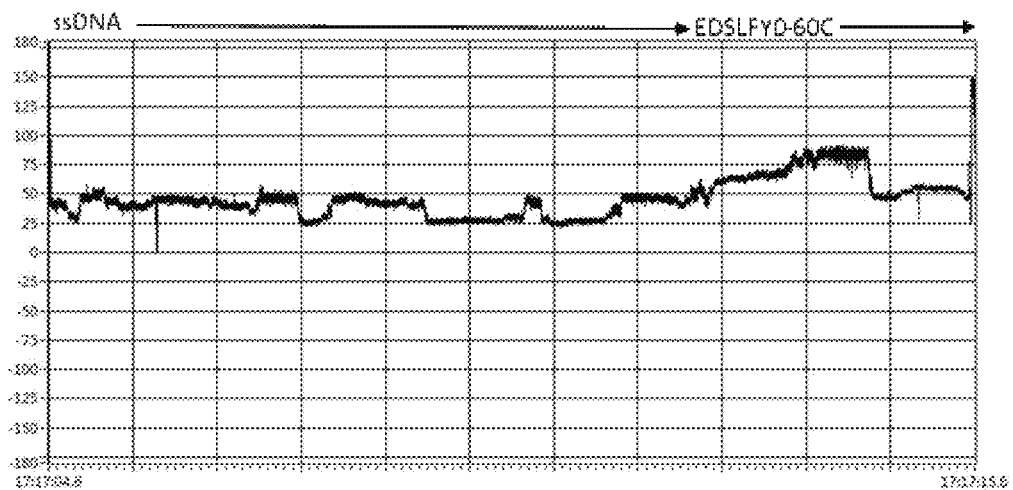
FIGS. 13-14 illustrate test results of the conjugate of ssDNA and EDSLFYD-60C.
Figure 14:
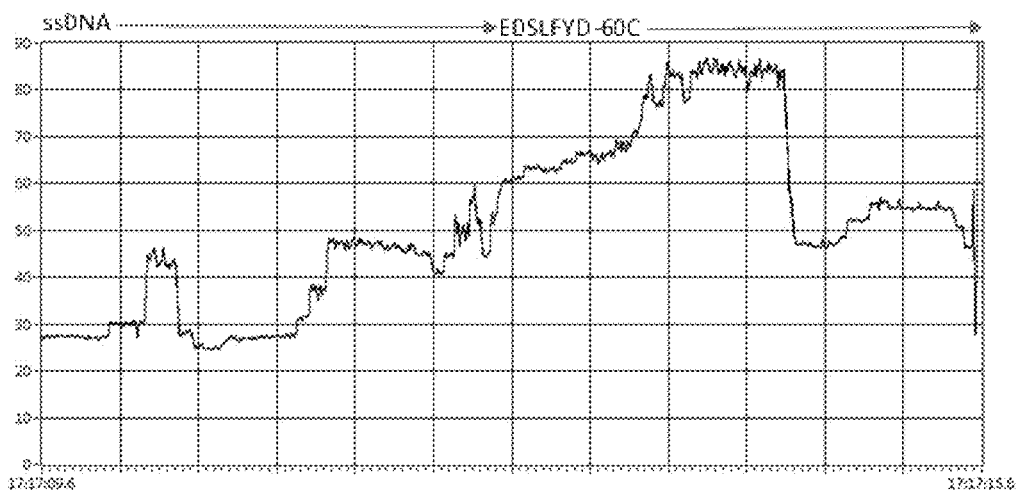

As shown in FIG. 13, the ssDNA-EGSLFL-60C conjugate first demonstrated a current signal similar to those in FIGS. 7 and 8, indicating a controlled passing-through of the ssDNA part. After this signal, the current continuously increased to a plateau at 80 pA before it decreased to 46 pA, increased to 55 pA and then decreased to 45 pA. This was caused by greater changes in sequence and species of the first 10-20 amino acids from the C-terminus to the N-terminus of the EGSLFL-60C peptide chain as compared to Example 4 and Example 5, thus resulting in more complex changes in current over time. FIG. 14 is an enlarged view of the signal in FIG. 13 where the peptide chain passed through the nanopore.

The preferred embodiments of the present invention are described in detail above, which, however, are not intended to limit the present invention. Within the scope of the technical concept of the present invention, various simple modifications can be made to the technical solution of the present invention, all of which will fall within the protection scope of the present invention.

In addition, it should be noted that the various specific technical features described in the above specific embodiments can be combined in any suitable manner without contradiction. In order to avoid unnecessary repetition, such combinations will not be illustrated separately.

Various embodiments of the present invention can also be combined arbitrarily, and should also be regarded as the disclosure of the present invention, as long as they do not violate the idea of the present invention.

The invention claimed is:

1. A method for controlling a speed of a polypeptide passing through a nanopore, comprising:
   1) conjugating the polypeptide to a polynucleotide to give a polynucleotide-polypeptide conjugate; and
   2) applying a voltage across the nanopore in the presence of a polynucleotide binding enzyme to move the polynucleotide-polypeptide conjugate through the nanopore, wherein the polynucleotide binding enzyme controls the movement of the polynucleotide, thus controlling the speed of the conjugated polypeptide passing through the nanopore.

2. The method according to claim 1, wherein the polynucleotide binding enzyme is a helicase, a polymerase or a translocase.

3. The method according to claim 2, wherein the polymerase is phi29 polymerase.

4. The method according to claim 2, wherein the helicase is an Hel308 family helicase.

5. The method according to claim 4, wherein the helicase is Hel308 Tga, Hel308 Mbu, Hel308 Pfu, Hel308Mma, Hel308Mok, Hel308Fac, Hel308Csy, Hel308Mhu, or F8813 protein.

6. The method according to claim 1, wherein the polynucleotide is a DNA or RNA.

7. The method according to claim 1, wherein the polynucleotide is a single-stranded DNA.

8. The method according to claim 1, wherein the polynucleotide and the polypeptide are linked covalently or through a linker group to form the polynucleotide-polypeptide conjugate.

9. The method according to claim 8, wherein the covalent linkage of the polynucleotide and the polypeptide is in a manner selected from an oxime bond, an amide bond, a thioether bond, a disulfide bond, a phosphoryl bond, a hydrazone bond, and a ureide bond, and a cyclic linkage formed by click reaction.

10. The method according to claim 1, wherein the nanopore is a biological nanopore or a solid nanopore.

11. The method according to claim 10, wherein the biological nanopore is selected from *Staphylococcus aureus* α-hemolysin nanopore, MspA nanopore, Csgg nanopore, phi29 nanopore and FraC nanopore.

12. The method according to claim 10, wherein the solid nanopore is selected from graphene nanopore, silicon nitride nanopore, titanium dioxide nanopore, and alumina nanopore.

13. A method for measuring an electrical signal of a polypeptide formed by the polypeptide passing through a nanopore sensor, comprising:
   1) conjugating the polypeptide to a polynucleotide to give a polynucleotide-polypeptide conjugate;
   2) applying a voltage across the nanopore in the presence of a polynucleotide binding enzyme to move the polynucleotide-polypeptide conjugate through the nanopore, wherein the polynucleotide binding enzyme controls the movement of the polynucleotide, thus controlling the speed of the conjugated polypeptide passing through the nanopore; and
   3) reading a nanopore current signal to acquire the electrical signal of the polypeptide.

14. The method according to claim 13, comprising:
   1) conjugating the polypeptide to a polynucleotide to give a polynucleotide-polypeptide conjugate;
   2) applying a voltage across the nanopore in the presence of a polynucleotide binding enzyme to move the polynucleotide-polypeptide conjugate through the nanopore, wherein the polynucleotide binding enzyme controls the movement of the polynucleotide, thus controlling the speed of the conjugated polypeptide passing through the nanopore; and
   3) reading a nanopore current signal to identify a current signal of the amino acid sequence of the polypeptide.

15. A method for identifying a polypeptide or a part thereof, wherein the identification is performed by measuring an electrical signal generated by the polypeptide passing through a nanopore sensor, comprising:
   1) ligating the polypeptide to a nucleic acid to give a nucleic acid-polypeptide ligation product;
   2) applying a voltage across the nanopore in the presence of a nuclease to move the nucleic acid-polypeptide ligation product through the nanopore, wherein the nuclease controls the movement of the nucleic acid, thus controlling the speed of the ligated polypeptide passing through the nanopore;
   3) reading a nanopore current signal to acquire the electrical signal of the polypeptide; and
   4) identifying the polypeptide or the part thereof based on the electrical signal.

16. The method according to claim 15, wherein the identification is to detect, in the polypeptide or the part thereof, a post-translational modification selected from ubiquitination, phosphorylation, glycosylation, esterification, alkylation and acetylation, glutamation, lipoation, isoprenylation, glycination, sulfation, adenylation and ADP ribosylation.

17. The method according to claim 15, wherein the part is a continuous amino acid sequence of the polypeptide.

18. The method according to claim 15, wherein the part is one or several amino acid residues of the polypeptide.

19. The method according to claim 15, wherein the part is one or more mutation sites of the polypeptide.

20. The method according to claim 15, wherein in step 4), the polypeptide or the part thereof is identified by comparing an electrical signal of the polypeptide with signals from a library of known polypeptides.

* * * * *

SEQUENCE LISTING

<160> NUMBER OF SEQ ID NOS: 5

<210> SEQ ID NO 1

```
<211> LENGTH: 99
<212> TYPE: DNA
<213> ORGANISM: Artificial Sequence
<220> FEATURE:
<223> OTHER INFORMATION: Synthetic construct

<400> SEQUENCE: 1
caagaatacc ttttttttc cttttttttc ctctaccact tttcagatct cactatcgca    60
ttctcatgca ggtcgtagct tttttctttt ttcatcatc                          99

<210> SEQ ID NO 2
<211> LENGTH: 75
<212> TYPE: DNA
<213> ORGANISM: Artificial Sequence
<220> FEATURE:
<223> OTHER INFORMATION: Synthetic construct

<400> SEQUENCE: 2
tttttttttt ttttgctac gacctgcatg agaatttttt tttttttttt tttttttttt    60
tttttttttt ttttt                                                    75

<210> SEQ ID NO 3
<211> LENGTH: 60
<212> TYPE: PRT
<213> ORGANISM: Artificial Sequence
<220> FEATURE:
<223> OTHER INFORMATION: Synthetic peptide

<400> SEQUENCE: 3

Glu Glu Glu Glu Gly Glu Glu Glu Gly Gly Glu Glu Glu Gly Gly
1               5                   10                  15

Glu Glu Glu Ser Ser Glu Glu Glu Gly Gly Glu Glu Glu Leu Phe
                20                  25                  30

Glu Glu Gly Gly Gly Gly Glu Glu Glu Ser Ser Ser Ser Glu Glu
            35                  40                  45

Glu Glu Leu Leu Glu Glu Glu Glu Glu Glu Glu Cys
        50                  55                  60

<210> SEQ ID NO 4
<211> LENGTH: 60
<212> TYPE: PRT
<213> ORGANISM: Artificial Sequence
<220> FEATURE:
<223> OTHER INFORMATION: Synthetic peptide

<400> SEQUENCE: 4

Glu Asp Glu Asp Glu Glu Glu Asp Tyr Asp Asp Glu Glu Glu Asp
1               5                   10                  15

Glu Glu Asp Glu Val Glu Glu Glu Glu Glu Tyr Gly Glu Val Val Gly
                20                  25                  30

Glu Leu Gly Gly Gly Gly Ser His His Asp His His Ser Ser Ser Gly
            35                  40                  45

Ser Glu Glu Glu Tyr Glu Glu Asp Asp Asp Asp Cys
        50                  55                  60

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide

<400> SEQUENCE: 5
```

```
Glu Glu Glu Glu Glu Glu Glu Glu Glu Glu Glu Glu Glu Glu Glu
1               5                   10                  15
Glu Glu Glu Glu Glu Glu Glu Glu Glu Glu Glu Cys
            20                  25              30
```